(12) United States Patent
Gutheil et al.

(10) Patent No.: US 7,214,769 B2
(45) Date of Patent: May 8, 2007

(54) METHOD FOR INVERSE SOLID PHASE SYNTHESIS OF PEPTIDES

(75) Inventors: William G. Gutheil, Kansas City, MO (US); Qingchai Xu, Sacramento, CA (US)

(73) Assignee: The Curators of the University of Missouri, Columbia, MO (US)

( * ) Notice: Subject to any disclaimer, the term of this patent is extended or adjusted under 35 U.S.C. 154(b) by 511 days.

(21) Appl. No.: 10/156,669

(22) Filed: May 23, 2002

(65) Prior Publication Data

US 2003/0027982 A1    Feb. 6, 2003

Related U.S. Application Data

(60) Provisional application No. 60/293,273, filed on May 23, 2001.

(51) Int. Cl.
 *C07K 1/04* (2006.01)
(52) U.S. Cl. .................. 530/333; 530/334; 530/335
(58) Field of Classification Search ............. 530/333, 530/334, 335
 See application file for complete search history.

(56) References Cited

FOREIGN PATENT DOCUMENTS

WO WO-90/05738 5/1990
WO WO-93/05065 3/1993

OTHER PUBLICATIONS

Matseuda (J. Am. Chem Soc. 97, 2573-75, 1975).*
Maruyama, Hiroshi (Bulletin of the Chemical Society of Japan 49(8), 2259-67, 1976).*
Matsueda, Rei, "Solid Phase Peptide Synthesis by Oxidation-Reduction Condenstation. Synthesis of LH-RH by Fragment Condensation on Solid Support", *Bulletin of the Chemical Society of Japan*, vol. 46, No. 10, (1973),3240-3247.
Rai, Aman, et al., "A Dde Resin Based Strategy for Inverse Solid-Phase Synthesis of Amino Terminated Peptides, Peptide Mimetics and Protected Peptide Intermediates", *Journal of Peptide Science*, (2004), 5.
Sasubilli, Ramakrishna, et al., "General Inverse Solid-Phase Synthesis Method for C-Terminally Modified Peptide Memetics", *J. Comb. Chem.*, 6, (2004), 911-915.
Gutheil, William.G. ,et al. ,"N-to-C Solid-Phase Peptide and Peptide Tirflouromethylketone Synthesis Using Amino Acid tert-Butyl Esters", *Chem. Pharm. Bull.* vol. 50, No. 5, (Feb. 20, 2002),688-691.
Xu, Qingchai.,et al. ,"A New Strategy for Inverse Solid-Phase Peptide Synthesis", *Peptides: The Wave of the Future; American Peptide Society*, 2001, 234-235.

\* cited by examiner

*Primary Examiner*—David Lukton
(74) *Attorney, Agent, or Firm*—Schwegman, Lundberg, Woessner & Kluth P.A.

(57) ABSTRACT

The present invention provides a process for preparing a peptide of formula (I):

$$\text{Sub-[L]-[NH-A-C(O)]}_{n+m}\text{—OH} \quad (I)$$

Figure 1:
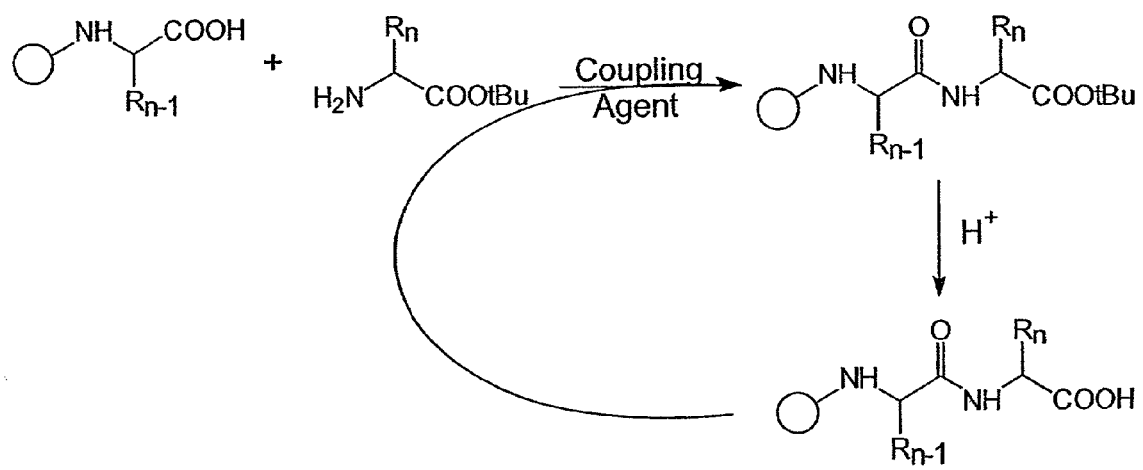

comprising:
(a) reacting an immobilized compound of formula (II):

$$\text{Sub-(L)-[NH-A-C(O)]}_{n}\text{—OH} \quad (II)$$

with an amino acid ester or peptide derivative of formula (III):

$$\text{H—[NH-A-C(O)]}_{m}\text{—O(tBu)} \quad (III)$$

in the presence of a coupling agent to yield a peptide compound of general formula (IV):

$$\text{Sub-[L]-[NH-A-C(O)]}_{n+m}\text{—O(tBu);} \quad (IV)$$

(b) removing the tBu (t-butyl) group to produce a solid-support bound carboxylic acid or peptide derivative of general formula (I);
wherein n is a positive integer, e.g., 1-10, preferably 1-5; m is a positive integer.

33 Claims, 4 Drawing Sheets

Reverse phase HPLC chromatogram of inverse peptide synthesized Suc-Ala-Leu-Pro-Phe.

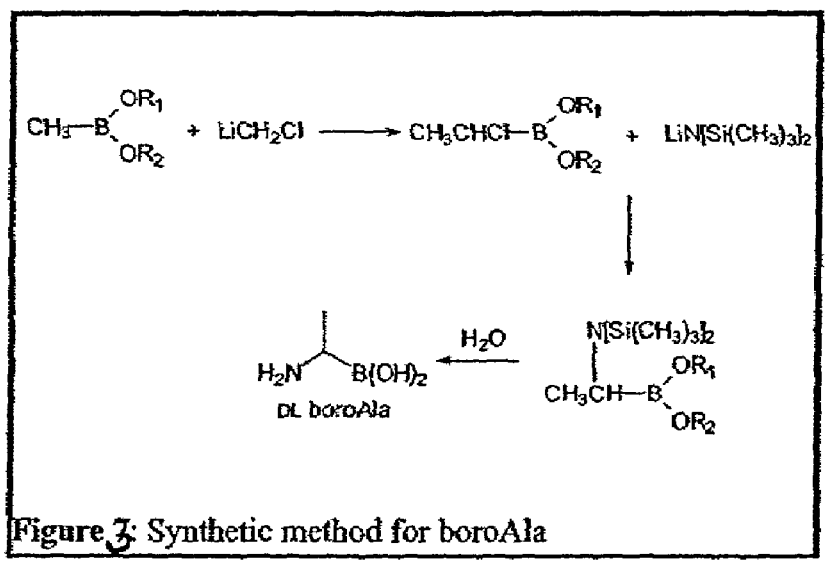
Figure 3: Synthetic method for boroAla
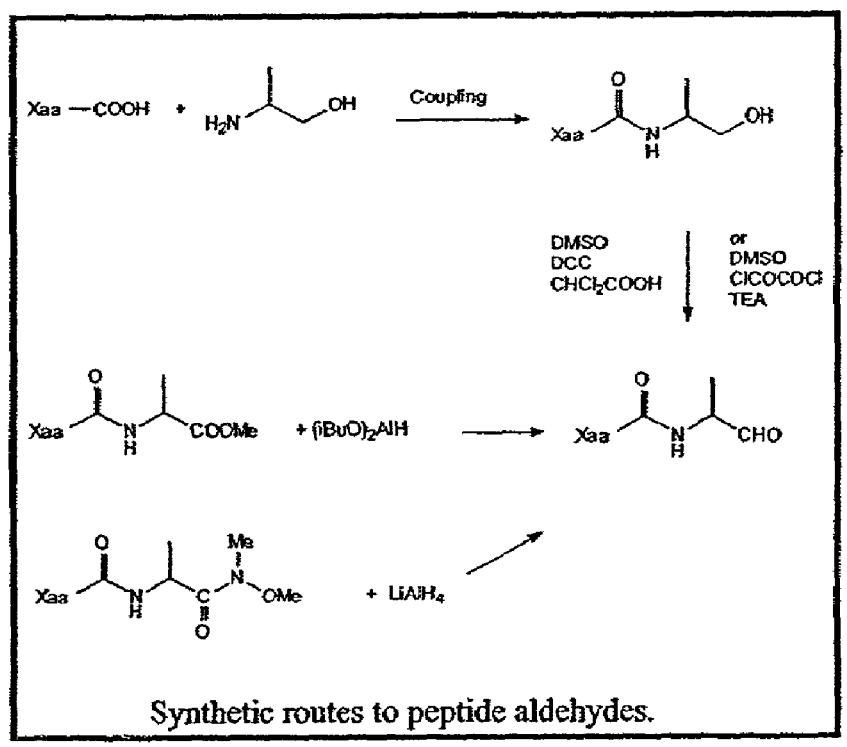
Synthetic routes to peptide aldehydes.
FIGURE 4.

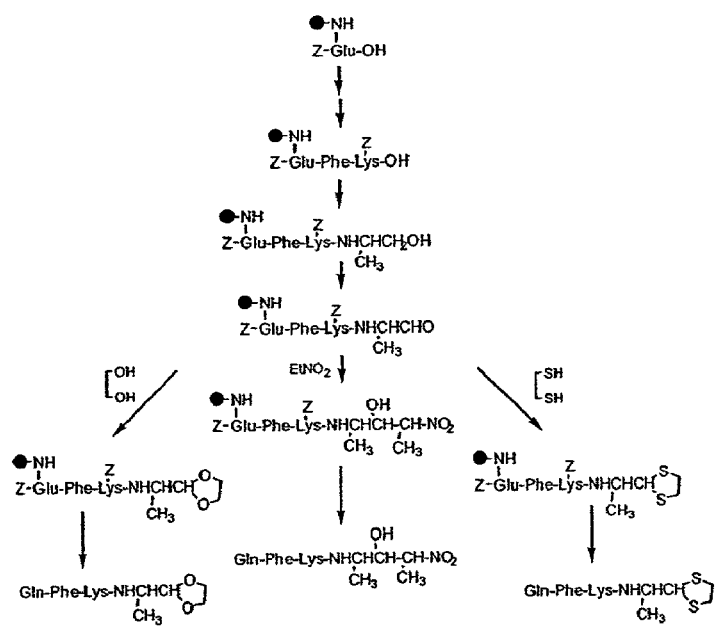
Figure 5: Synthesis, protection, and derivatization of inverse peptide aldehydes.
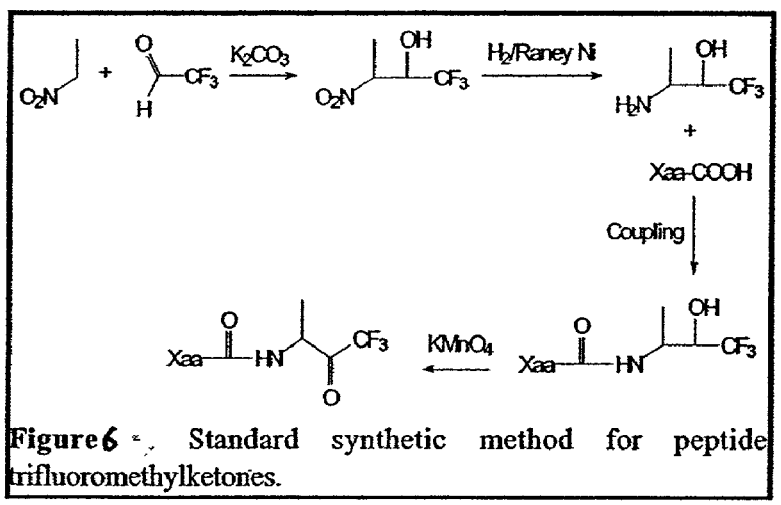
Figure 6: Standard synthetic method for peptide trifluoromethylketones.
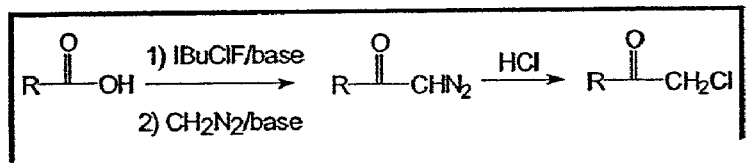
FIGURE 7.

SEQUENCE LISTING

<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: A synthetic succinylated peptide

<400> SEQUENCE: 1

Ala Leu Pro Phe
1

METHOD FOR INVERSE SOLID PHASE SYNTHESIS OF PEPTIDES

This application claims the benefit of U.S. Provisional Application No. 60/293,273, filed May 23, 2001.

This invention was made with support of the National Institutes of Health under Grant No. GM60149. The U.S. Government has certain rights in this invention.

BACKGROUND OF THE INVENTION

The standard methods for the solid phase synthesis of peptides (SPPS) on beaded resins in the normal C-to-N direction are well developed, as they must be if long peptides are to be synthesized (reviewed in M. Bodanszky et al., "Peptide Chemistry: A Practical Textbook," Springer-Verlag, N.Y. (2d ed., 1993) and M. Bodanszky et al., "The Practice of Peptide Synthesis," Springer-Verlag, N.Y. (2d ed., 1993)). These methods are based on attaching the carboxy terminus of an amino-protected amino acid to the resin. It essentially allows peptides to be synthesized without racemization when amino acids with $N^\alpha$-protecting groups of the urethane (carbamate) type were coupled in stepwise fashion. The amino-protecting group is removed, and the next amino acid with a free carboxy group and protected amino group is then added using standard coupling conditions. Standard peptide chemistry has been used to prepare solid phase peptide libraries of tremendous diversity (H. M. Geysen et al., *Molec. Immunol.*, 23, 709 (1986); R. A. Houghten et al., *Nature*, 354, 84 (1991); K. S. Lam et al., *Nature*, 354, 84 (1991)).

Peptide mimetic libraries (mimetic is used to indicate a modified peptide), based on the normal C-to-N direction of peptide synthesis, have been described. A peptide phosphinate library has been synthesized and used to find potent and selective inhibitors of zinc metalloproteases (J. Jiracek et al., *J. Biol. Chem.*, 270, 21701 (1995); J. Jiracek et al., *J. Biol. Chem.*, 271, 19606 (1996); V. Dive et al., *PNAS USA*, 96, 4330 (1999)). A (hydroxyethyl)amine library has also been synthesized and used to find inhibitors of the prototypical aspartyl protease Cathepsin D (E. R. Kick et al., *Chem. Biol.*, 4, 297 (1997)).

However, combinatorial libraries of polypeptides representative of serine and cysteine proteases have not been synthesized. This can be attributed to the fact that virtually all the effective classes of serine and cysteine classes, such as peptide aldehydes (R. C. Thompson, *Biochem.*, 12, 47 (1973)), chloromethyl ketones (CMKs) (G. Schoellmann et al., *Biochem.*, 2, 252 (1963)), fluoromethyl ketones (FMKs) (M. H. Gelb et al., *Biochem.*, 24, 1813 (1985); B. Imperiali et al., *Biochem.*, 25, 3760 (1986)), and boronic acids (C. A. Kettner et al., *J. Biol. Chem.*, 259, 15106 (1984); C. A. Kettner et al., *J. Biol. Chem.*, 265, 18289 (1990)), are prepared by elaboration of a peptide at its C terminus. Thus, a need exists for the development of combinatorial peptide libraries representative of the serine and cysteine protease classes. Such libraries would greatly improve the ability to develop potent and specific inhibitors of these enzymes. This, in turn, requires a free C terminus of an immobilized oligopeptide, which, in turn, requires the ability to synthesize peptides in the N-to-C direction: or "reverse peptide synthesis."

Considering the importance of such C-terminally modified peptides and peptide libraries, relatively few reports have been devoted to the development of a direct method for peptide assembly in the inverse direction. See, for example, R. J. Broadbridge et al., *Chem. Commun.*, 1449 (1998), K. H. Bleicher et al., *Tett. Lett.*, 39, 4591 (1998); F. Bordusa et al., *Angew Chim Int. Ed. Eng.*, 36, 1099 (1997); R. Leger et al., *Tet. Lett.*, 39, 4147 (1998); R. Letsinger et al., *J. Amer. Chem. Soc.*, 85, 5163 (1969); and 85, 3015 (1963).

Merrifield et al., *J. Amer. Chem. Soc.*, 92, 1385 (1970), used protected amino acid hydrazides as building blocks for the C-terminal elongation of peptides, followed by deprotection and subsequent reaction of the hydrazide function with nitrite allowed the next building block to be coupled by the azide method. However, the procedure is elaborate, requiring activation and coupling at low temperature with moderate yields.

Later investigations, mainly by Bayer and co-workers, have included the use of base labile amino acid 9-fluorenylmethyl esters, which were coupled with N-hydroxybenzotriazole (HOBt)/diisopropylcarbodiimide (DIC) or N-[(1H-benzotriazole-1-yl)-(di-methylamino)methylene]-N-methylmethanaminium tetrafluoroborate N-oxide (TBTU)/N-methylmorpholine (NMM). B. Henkel et al., *Liebigs Ann./Recieul*, 2161 (1997). In both cases, a 30-min. preactivation step with a large excess of activator (8 equiv.) was included before addition of the amino acid ester. Using TBTU/NMM extensively racemized products were obtained, whereas coupling using HOBt/DIC gave moderate racemization but led to significant formation of other byproducts.

Sharma et al. have described a few C-terminally modified tetrapeptide HIV-1 protease inhibitors, generated in the inverse direction. For example, see, R. P. Sharma et al., published PCT applications WO 93/05065 (18 Mar. 1993) and WO 90/05738 (31 May 1990) and *Chem. Commun.*, 1449 (1998). Sharma's approach relies on coupling of amino acid tri-tert-butoxysilyl (Sil) esters. More recently, A. Johannsson et al., *J. Comb. Chem.*, 2, 496 (2000) described a modification of the method of Sharma et al. that involves the coupling of a photolabile resin-bound C-terminal amino acid with excess amounts of amino acid tri-tert-butoxysilyl (Sil) esters, using HATU as coupling reagent and 2,4,6-trimethylpyridine (TMP, collidine) as a base. Levels of epimerization were considerably lower than those reported for other N-to-C methods, usually ca. 5% and occasionally even below 1%. However, in unfavorable cases, as in the coupling of Ile to Ser, the level was higher (ca. 20%). Also, this method requires the synthesis of sensitive zwitterionic tris (t-butoxy silylesters) and familiarity with photolytic techniques.

Thus, a continuing need exists for simple and efficient methods for the reverse synthesis of peptides and peptide mimetics, particularly for the synthesis of oligopeptide mimetic libraries useful for high-throughput drug screening.

SUMMARY OF THE INVENTION

The present invention provides a process for preparing a peptide of formula (I):

comprising:

(a) reacting an immobilized compound of formula (II):

with an amino acid ester or peptide derivative of formula (III):

in the presence of a coupling agent to yield a peptide compound of general formula (IV):

Sub-[L]-[NH-A-C(O)]$_{n+m}$—O(tBu)　　(IV);

(b) removing the tBu (t-butyl) group to produce a solid-support bound carboxylic acid or peptide derivative of general formula (I);

wherein n is a positive integer, e.g., 1–10, preferably 1–5; m is a positive integer, e.g., 1–10, preferably 1–5. Sub is a solid support such as a polymer or glass substrate, preferably comprising free OH, or NH$_2$ groups. L is a linker to the amino acid ester or peptide derivative. Each A independently is the residue of a naturally occurring or synthetic amino acid; a peptide residue, such as an oligopeptide or polypeptide; or the structure —NH-A represents a heterocyclic group, e.g., a C$_5$–C$_{10}$ heterocyclic group comprising 1–2 O, N and/or S such as pyrrolidine, indole or imidazole. This approach is summarized in FIG. 1, wherein CHR represents the residue of an α-amino acid and O represents Sub.

The present method optionally comprises, prior to step (a): forming a solid-support bound compound of general formula (VI):

Sub-[L]-[NH-A-C(O)]$_n$—O(tBu)　　(VI);

by reacting a functionalized solid support of general formula Sub[L]X with a compound of formula: H—[NH-A-C(O)]$_n$—OH, wherein X is a group such as CO$_2$H, or an activated carboxylic acid ester, that links L to NH$_2$-A by elimination of XH; and removing the t-Bu group to yield a compound of formula (II). Preferred moieties [L]X include —OC(O)(CH$_2$)$_2$CH(NHZ)CO$_2$H, HNC(O)(CH$_2$)$_2$CH(NHZ)CO$_2$H, and —C(O)(CH$_2$)$_2$CO$_2$H, wherein Z is H or an amino group protecting group such as benzyloxycarbonyl (Cbz).

The present method preferably further comprises the step of cleaving compound (IV) at the L-NH bond to yield a compound of formula (IX):

H—[HN-A-C(O)]$_{n+m}$—OH.　　(VIII)

or of cleaving compound (IV) at the Sub-(L) bond to yield a compound of formula (X):

H-(L)-[NH-A-C(O)]$_n$—O(tBu)　　(X), wherein the amino group protecting groups are then removed, as necessary.

The present method preferably further comprises, following step (b); carrying out, x times, the steps of reacting compound (I) with a compound of formula (III) and removing the tBu group to yield a compound of formula (VIII):

Sub-(L)-[NH-A-C(O)]$_{n+m(x+1)}$—OH　　(VIII).

For example, if n and m are both 1, and A is an amino acid residue, carrying out the steps 3 times will yield an immobilized oligopeptide having 5 peptidyl residues, not including L. The values n+m(x+1) can be any integer up to the maximum number of residues yielding a useful polypeptide or polypeptide analog, e.g., about 75–100. Compound (VIII) can also be cleaved at the sub-(L) bond or the (L)-NH bond to yield compounds analogous to compounds (IX) and (X) above.

Novel compounds, particularly immobilized peptides, are also within the scope of the present invention, e.g., compounds (I), (II), (III), (IV), (VI), (VIII) and the like.

Preferably, each A is individually the residue of an α-amino acid, most preferably, a residue of a naturally occurring L-amino acid, such as the alkylidenyl or substituted alkylidenyl residues derived from glycine (Gly) (—CH$_2$—), alanine (Ala)

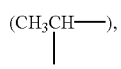

serine (Ser)

threonine (Thr)

valine (Val)

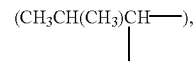

leucine (Leu)

isoleucine (Ile)

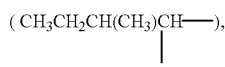

cysteine (CySH)

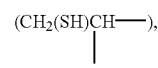

cystine (CyS—SCy)

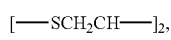

phenylalanine (Phe)

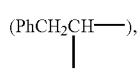

tyrosine (Tyr)

proline (Pro) (pyrrolidin-2-yl), hydroxyproline (4hydroxy-2-pyrrolidinyl), tryptophan (Trp)

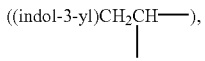

aspartic acid (Asp)

glutamic acid

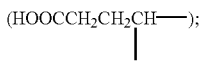

histidine (His)

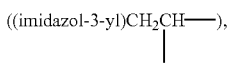

lysine (Lys)

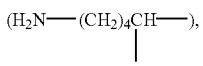

or arginine (Arg)

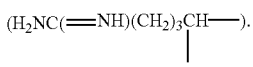

Free $CO_2H$, $NH_2$, OH, or SH groups on A groups can optionally be protected with suitable protecting groups (Z) such as tBoc, Cbz, acyl, benzyl, silyl, hemiacetals, or alkyl.

The present method can also be readily adapted to form C-terminal modified peptides, for example, by reacting compound (I) or (VIII) with $H_2N(alkyl)CH(OH)CF_3$ to yield the corresponding amide of (I) or (VIII) and oxidizing the CH(OH) moiety to yield a trifluoromethyl ester of general formula:

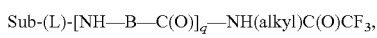

wherein q is n+m or n+m(x+1), respectively, followed by cleaving the compound from Sub to yield a compound of formula:

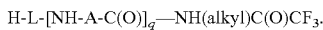

Compound (I) or (VIII) can also be reacted with $H_2N$(alkyl)OH to yield the hydroxyalkylamide of (I) or (VIII) and oxidizing the terminal hydroxy group to yield a terminal aldehyde of formula:

Sub-(L)-[NH-A-C(O)]$_q$—NH(alkyl)CHO.

The terminal CHO group can be protected by conversion into an ethylene glycol acetal, a propylene glycol acetal, an ethylene dithiol acetal or a 1,3-dithiane, and cleaved from the substrate

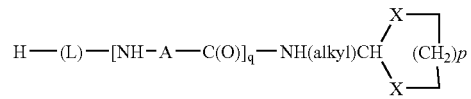

wherein X is O or S, and p is 0 or 1. The group (alkyl) is preferably a ($C_1$–$C_6$) alkyl moiety, including the alkylidenyl or substituted alkylidenyl moieties described hereinabove.

Compound (I) or (VIII) can also be reacted with a boroamine to yield a compound of formula:

Sub-[L]-[NH-A-C(O)]$_q$—NH(A)B(OR)$_2$ wherein R is ($C_1$–$C_6$)alkyl, phenyl or the residue of an organic diol such as pinanediol, catechol, pinacol, diethanolamine and the like. See, Kettner (U.S. Pat. No. 4,499,082). R can be cleaved from Sub to yield a compound of the formula:

H-[L]-[NH-A-C(O)]$_q$—NH(A)B(OH)$_2$.

As noted above, in some cases, it is desirable to cleave the [L]-NH bond of Sub-[L]-NH to free the peptide from Sub.

The corresponding terminal chloromethyl ketone, C(O)CH$_2$Cl, can be prepared from the free CO$_2$H compounds as disclosed below.

In accord with the present method, reversing the direction of peptide synthesis provides the chemically versatile carboxy group for modification. This approach has significant advantages for preparing solid phase peptides with either a free carboxy terminus or a carboxy terminal peptide mimetic. These advantages include:

1) The ability to prepare immobilized peptides with a free carboxy terminus;
2) The ability to prepare immobilized peptides with a directly modified carboxy terminus, for example, peptide esters, peptide aldehydes, and peptide chloromethyl ketones; and
3) The ability to introduce other monomer groups, such as amino acid mimetics such as boronic acids and trifluoromethyl ketones, onto the carboxy terminus.

Such derivatives, such as peptide aldehydes and chloromethyl ketones, can themselves serve as intermediates during the syntheses of other derivatives. For example, peptide chloromethyl ketones can be treated with nucleophilic reagents, which will displace the chloride ion, to make further derivatives. The same applies to peptide aldehydes. This synthetic versatility of the carboxy group allows tremendous chemical diversity to be accessed via the inverse N-to-C peptide synthesis method described here.

As prepared in accord with the present method, peptide and peptide mimetic libraries can be screened for drug leads for nearly any desired target. The present invention can provide a novel set of peptide mimetic libraries for use in such screens. Most notably, this invention provides a way to generate chemical substances of particular interest for the discovery of potent and specific protease inhibitors, especially the serine and cysteine proteases. Most protease inhibitor classes are based on carboxy group chemistry. Examples include peptide boronic acids, peptide aldehydes, peptide chloromethyl ketones, and peptide fluoromethyl ketones. Proteases dependent diseases which can be targeted using such compounds include hepatitis, AIDS, Alzheimer's disease, malaria and cancer, among others. The penicillin-binding proteins (PBPs) are also excellent targets for this synthetic method since they require a free carboxy terminus. New PBP inhibitors also are candidates as new antibacterial agents.

DETAILED DESCRIPTION OF THE INVENTION

The present method provides a simple and effective method for synthesizing peptides in the N-to-C direction, based on amino acid t-butyl esters, as shown in FIG. 1. This method takes advantage of the availability of a number of amino acid t-butyl esters, and a list of commercially available amino acid t-butyl esters appropriate for reverse peptide synthesis is given in Table 1. This list provides suitable derivatives to prepare L peptides containing all the standard L amino acids except Asp, Cys, Ser, and thr, as well as a number of non-standard and D amino acids.

TABLE 1

Commercially available amino acid t-butyl esters available from Bachem appropriate for N-to-C peptide synthesis.

| Ala-OtBu | Gln-OtBu | D-Leu-OtBu | D-Pro-OtBu |
|---|---|---|---|
| D-Ala-OtBu | Glu(OMe)-OtBu | Lys(Z)-OtBu | Sar-OtBu |
| β-Ala-OtBu | Glu(OtBu)NH$_2$ | Met-OtBu | Thr-OtBu |
| Arg(Mtr)-OtBu | Gly(OtBu)-OMe | Orn(Z)-OtBu | Trp-OtBu |
| Asn-OtBu | Gly-OtBu | Phe-OtBu | Tyr-OtBu |
| Asp(OtBu)-NH$_2$ | His(1-Trt)-OtBu | Phg-OtBu | D-Tyr-OtBu |
| Asp(OtBu)-OMe | Ile-OtBu | Pro-OtBu | Val-OtBu |
|  | Leu-OtBu |  | D-Val-OtBu |

All amino acids are L unless otherwise indicated. Abbreviations: Standard amino acids have their normal abbreviations. Other Abbreviations: Mtr = 4-methoxy-2,3,6-trimethylbenzenesulfonyl, Orn = ornithine (2,5-diaminopentanoic acid), OtBu = O-t-butyl, Phg = L-phenylglycine, Sar = sarcosine (N-methyl glycine), Trt = trityl.

A number of conditions are expected to affect both coupling efficiency and quality (racemization) of the final product. Syntheses can be monitored for overall yield by HPLC and for racemization using Marfey's reagent (Marfey, Calsberg Res. Commun., 49, 591 (1984); Adamson et al., Anal. Biochem., 202, 202 (1992)). Optimization can be performed for the coupling of Pro to Suc-Phe-Leu, since addition of Pro should be more difficult than most amino acids, and coupling to a dipeptide (Suc is the linker) allows racemization both at the activated residue (Leu in this case) (Bodanski cited above (1993)). Phe can provide a convenient chromophore for detection of products.

In normal (C-to-N) peptide synthesis, an excess of the activated carboxyl component is used to drive the reaction to completion. In N-to-C synthesis, the carboxyl group is anchored and cannot be generated in excess. This problem can be solved by using carbodiimides, or other coupling reagents, which can be used in the presence of the carboxyl component and an excess of the amine component. A second difficulty concerns which protection chemistry to use for the carboxyl group of the amine component. One recent report (Johansson et al., cited above (2000)) describes the use of amine components with a silyl-protected carboxyl group, the use of a photolabile attachment to the solid support, and the use of HATU, (O-(7-Azabenzotriazol-1-yl)-N,N,N',N'-tetramethyluronium hexafluorophosphate; or TATU (O-Benzotriazol-1-yl-N,N-N',N'-tetramethyluronium tetrafluoroborate) as coupling agents. HBTU, and PyBOP can also be used as coupling agents.

These reagents can be used in about 2, 4, 6, and 8-fold molar excess. Bases 2,4,6-trimethylpyridine (TMP), diisopropyl amine (DIEA), and N-methylmorpholine (NMM) can be used at 2.5, 5, 7.5, or 10-fold molar excess as in the standard peptide coupling method. The amino acid concentration can be used in 2.5, 5, 7.5, or 10-fold molar excess over the base concentration. Mixtures of CH$_2$Cl$_2$/DMF of 8:0, 7:1, 6:2, 5:3, 4:4 of 0:8, can be employed as solvents. In some cases, a linker which would "disappear" upon removal of the peptide from the substrate, can be used.

A free N-terminal amino group as is generated by cleavage of the immobilized peptides, using Glu or Gln linkers can provide an anchor for attaching peptides made with this strategy to glass slides or silicon wafers, which would allow very high throughput screening of libraries using microarray spotting and reading technology which has been developed for genomics studies.

The extent of coupling is currently qualitatively assessed by testing for free carboxyl groups using Malachite Green (Attardi et al., Tet. Lett., 41, 7391 (2000)), analogous to the use of ninhydrin to test for free amines. In some cases, sequence data from peptides might be useful and effective approaches for C-terminally sequencing peptides (succinylated peptides in solution and solid phase) are now available (Samyn et al., Anal. Biochem., 72, 1389 (2000)).

These different resins have been tested—hydroxymethyl polystyrene and Pam resin (4-hydroxymethylphenylacetamidomethyl polystyrene) and MBHA. To provide the initial carboxyl group, a succinyl linker was used in preliminary studies. Some loss of polypeptide was observed during TFA (trifluoroacetic acid) deprotection of t-butyl esters on hydroxymethyl polystyrene resin, but not significantly with Pam resin, and Pam resin was used in subsequent studies. MBHA forms an amide linkage with the Glu linker that cleaves to an N-terminal glutamine (Glu) residue on the free peptide.

The initial coupling strategy used a five-fold excess of amine and coupling reagent. Excess coupling reagent and amine can be washed away after coupling is complete. A number of such coupling reagents are known. Three have been tested to date: HATU, dicyclohexylcarbodiimide (DCC)/hydroxybenztriazol (HOBT) and O-Benzotriazol-1-yl-N,N,N',N'-tetramethyl uronium hexafluorophosphate (HBTU). The coupling methods have been tested by comparison of synthesis of the succinylated peptide Suc-Ala-Leu-Pro-Phe (SEQ ID NO:1).

EXAMPLE 1

Preparation of Oligopeptide Using Succinylated Resin

Figure 2:
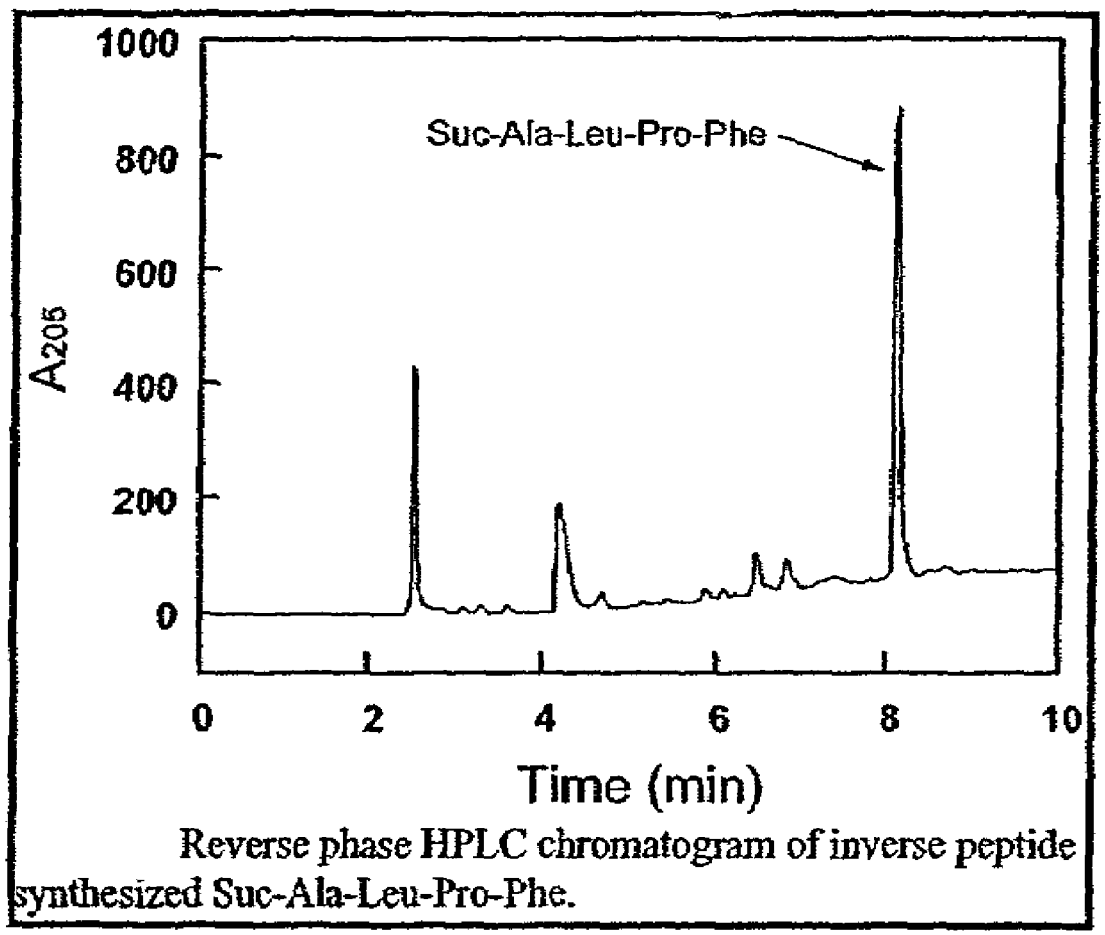

Starting with commercial Pam resin, the resin was first succinylated using succinic anhydride to provide a carboxyl group for subsequent coupling steps. Succinylation was selected for initial work since many protease related synthetic peptides are prepared with an N terminal succinyl group. Succinylated resin was then subjected to HBTU-mediated coupling of L-Ala-OtBu (L-Ala-t-butyl ester). Subsequently, the t-butyl ester was deprotected with 25% TFA/DCM (1×5 seconds, filter, then 1×30 min). This process was repeated with each subsequent amino acid t-butyl ester (Ala, Pro, Phe to give Suc-Ala-Leu-Pro-Phe; SEQ ID NO:1). Finally, the peptide was liberated from the polymer using TFMSA (trifluoromethylsulfonic acid)/TFA cleavage. The final product (FIG. 2) was the desired product, and its identity was confirmed by HPLC-MS comparison with commercially available authentic Suc-Ala-Leu-Pro-Phe (SEQ ID NO:1).

EXAMPLE 2

Comparison of Coupling Agents and Linkers

Using the Marfey's reagent based method cited above, HBTU and HATU coupling procedures have been compared for synthesis of the test peptide Suc-Ala-Leu-Pro-Phe as summarized in Table 2.

TABLE 2

| % D-isomer found in peptide Suc-Ala-Leu-Pro-Phe | | | | |
|---|---|---|---|---|
| | Ala | Leu | Pro | Phe |
| HBTU-coupling | 27% | 23% | <2% | <2% |
| HATU-coupling | 38% | 5% | <2% | <2% |

With both coupling procedures >20% racemization of the first residue attached to a succinyl linker is observed. HATU provides more effective coupling in general than HBTU or DCC, and HATU shows ≦5% racemization of subsequent residues even for the more difficult proline coupling. The observation of high racemization of only the first residue following the succinyl linker suggests that a protected α-amino group in a linker might reduce racemization of the first added residue.

Z-Glu-OtBu was therefore tested as a linker. Z-Glu-OtBu was coupled to PAM resin using the standard HATU-based coupling protocol, followed by the standard deprotection and coupling procedure. This modification resulted in <5% racemization of the residues in synthesized peptides. Peptides synthesized with this linker strategy have a Glu residue as the N-terminus (Glu linker strategy). To avoid the possibility of esterolytic cleavage of the resin-Glu attachment, we have also tested the use of an amide attachment strategy by coupling Z-Glu-OtBu to MBHA resin, a resin generally used in normal direction peptide synthesis to general C-terminally amidated peptides. Cleavage from this resin provides an N terminal Gln residue (i.e., amidated Glu side chain) (Gln linker strategy). This linker strategy also provided peptides with low (<5%) racemization in test syntheses. The increased stability of an amide link to the resin may prove useful for some carboxyl group modification methods. One advantage of both the Glu and Gln linker strategies over the succinyl linker strategy is that they provide the free N-terminal α-amino group of the terminal Glu or Gln residue which could be used to attach a multiplicity of peptides to derivatized substrates such as to silicon wafers or glass slides comprising free CHO groups, to yield "chip" libraries useful for very high throughput screening (cf., MacBeath and Schreiber, *Science*, 289, 1760–176 (2000)).

EXAMPLE 3

Inverse Peptide Synthesis Using MBHA Resin

MBHA-Z-Glu-OtBu resin (linked between the γ-carboxyl of Z-Glu-OtBu and the amine of MBHA resin) was employed. MBHA is a 4-methyl-benzhydryl amine polystyrene resin. The coupling method used is the HATU/TMP-mediated activation. Details of this method are described below.

1. Attachment of the Linker (Z-Glu-OtBu)

MBHA resin (1.0 equiv.) is first washed with DMF, 20% DIEA/DMF, DMF and DCM. To this pre-washed resin, a solution of Z-Glu-OtBu (5.0 equiv.) wherein Z is benzyloxycarbonyl, HATU (5.0 equiv.) and TMP (5.0 equiv.) in DMF is added. The suspension is stirred at room temperature for 3 h. The resin is then filtered and washed with DMF and DCM. The resulting resin is treated with a solution of acetic anhydride (3.0 equiv.) and DIEA (3.0 equiv.) in DMF for 30 min (to cap any remaining on-resin amine groups). The resin is filtered and washed with DMF and DCM.

2. Deprotection of tBu Group

Above resin is treated with 25% TFA in DCM (1×5 s) and 50% TFA in DCM (30 min×1). The resin then is washed with DCM×3, NMP×2, DCM×3, dried.

3. On-resin Assembly of Peptide-chain

The Z-Glu-linked resin is treated with a solution of an amino acid OtBu ester (5.0 equiv. usually HCl salt), HATU (5.0 equiv.) and TMP (10.0 equiv., 5 equiv. if amino acid is free base and not HCl salt) in DMF. The suspension is stirred at room temperature for 2 h. The resin is then filtered and washed with DMF and DCM. A small amount of resin sample (1~5 mg) is removed and subjected to a color test reaction using 1 ml of 0.25% Malachite Green (in ethanol) along with 1 drop of triethylamine. A double coupling is performed if the testing shows positive (green or blue on resin). If the testing gives negative result (no color on resin), then repeat step 2 and step 3 until reaching the desired length of peptide.

4. Cleavage of Peptide from the Resin

Before cleavage, the C-terminal protecting group (t-Bu) needs to be removed using the identical procedure described in step 2. After being washed and dried, the deprotected peptide-resin is treated with a mixture of TFA (100 μl) and TFMSA (10 μl) for about 1 h. The solution (crude product) is collected by filtration and is ready for HPLC and LC/MS analysis.

EXAMPLE 4

Introduction of Common Inhibitor Functional Groups, Such as Peptide Aldehyde, Chloromethyl Ketone, Fluoromethyl Ketone, and Boronic Acid, onto the C Terminus of Solid Phase Attached N-to-C Peptide Chains In preliminary studies, solution phase methods have been used to synthesize a representative example of each of these inhibitor classes. For solid phase syntheses, two distinct strategies will be required for this set of four inhibitor classes.

In the case of boronic acids and trifluoromethylketones, suitably derivatized inhibitor monomers must be prepared and introduced into the peptide chain. In the case of chloromethylketones and aldehydes, direct chemical modification of the C terminus can provide the desired functional group. Alanine is the naturally preferable P1 residue for the PBPs, and an acceptable residue for HLE.

A. Boronic Acid (boro-Ala) Based Peptides (—X—Y-Z-boroAla)

The chemistry required to prepare boroAla and several other hydrophobic amino acid analogs such as boro Val is well known (Kettner & Shenvi, *J. Biol. Chem.*, 259, 15106 (1984); Matteson & Sadhu, U.S. Pat. No. 4,525,309 (1985)). See FIG. 3. Boro-Ala can be introduced onto the C-terminus of a peptide using the standard procedures for adding an amino acid to a chain.

B. Peptide Aldehyde Based Peptides (—X—Y-Z-CHO)

As shown in FIG. 4, several strategies for the synthesis of peptide aldehydes have been described, including from amino alcohols by oxidation (Thompson, *Biochem.*, 12, 47 (1973); Okura & Swern, *Tetrahedron*, 34, 1651 (1978)), by reduction of the amino acid methyl esters with diisobutyla-luminum hydride (DIBAL) (Ito et al., *Biochem. Biophys. Res. Comm.*, 49, 343 (1975); Gorenstein & Shaw, *Biochem.*, 21, 4679 (1982)), or by reduction of Weinreb N-methoxy-N-methylcarboxamides with $LiAlH_4$ (Fehrentz & Castro, *Synthesis*, 676 (1983)). The best solution phase method tested so far is reduction of Weinreb amides. This method works well in the presence of Boc and Cbz groups, but may be incompatible with most esters.

There are a number of reducing agents of varying strength (Hudlicky, *Reagents In Org. Chem.*, ACS, (2d ed. 1998)) which can be applied to this problem. Several reducing agents of different power can be tested against a series of esters. Of particular interest is the possibility of generating active HOBT or HOAT esters, as is generated in the standard coupling reaction, and reducing them with a relatively mild reducing agent such as $LiAlH(OtBu)_3$. The possible coordinating effect of the active ester could facilitate such a reaction and assist in stopping the reaction at the aldehyde stage as occurs in reduction of Weinreb amides with $LiAlH_4$, possibly without reduction of side chain protected esters. Such a strategy should allow solid phase peptide aldehyde preparation via a simple modification of the standard reverse peptide synthesis strategy.

The successful Pfitzner-Moffat oxidation (DCC/$Cl_2HCO_2H$/DMSO) of the peptide trifluoroamino alcohol suggests this strategy could also work for synthesis of peptide aldehydes as outlined in FIG. 4. This approach was tested, and works well in generating an on resin aldehyde, but substantial degradation of the peptide aldehyde occurs during TFMSA/TFA cleavage from the resin. Protection of the aldehyde by treatment with a 20-fold excess of ethylene glycol in 5% TFA/DCM followed by cleavage from the resin provided the protected aldehyde (Gln-Phe-Lys-Ala-CH$(OCH_2)_2$ as the major peptide product ([M+H]=522.8). Impurities were: a) Gln-Phe-Lys ([M+H]: 421.5) due to incomplete coupling of the amino alcohol, b) Gln-Phe-Lys-Ala-CH$_2$OH([M+H]: 486.6), due to incomplete oxidation of the amino alcohol, and c) an unknown impurity ([M+H]: 574.8). Reaction of on resin peptide aldehyde with nitroethane and dithioethane have also been tested and give complete conversion of the aldehyde to the expected derivatives (FIG. 5). In FIG. 5, Z=benzyloxycarbonyl, •=resin, and Z-Glu-OtBu is PhCH$_2$OC(=O)NHCH(CH$_2$CH$_2$CO$_2$H)—CO$_2$tBu.

A large number of commercially available nucleophiles (cf. nitroethane) can be reacted with on-resin aldehydes to provide peptide aldehyde adduct libraries of tremendous diversity. Dithiane and other derivatives provide the further possibility of acyl-anion equivalent chemistry, which would allow peptide aldehydes to be further elaborated using various alkylating agents into peptide mimetic ketones (see, Seebach et al., *J. Org. Chem.* 40, 231 (1975); Hase et al., *Aldrichimica Acta*, 14, 73 (1981).

C. Trifluoromethylketone-based Peptides (X—Y-Z-Ala-CF$_3$)

The classic procedure for preparing peptide trifluoromethylketones is shown in FIG. 6 (Imperiali & Abeles, *Tet. Lett.*, 22, 135 (1986)). Oxidation of the acyl trifluoromethyl aminoalcohol was performed with $KMnO_4$, but can also be performed with a modified Pfitzner-Moffat (carbodiimide/$Cl_2HCO_2H$/DMSO) procedure (Fearon et al., *J. Med. Chem.*, 30, 1617 (1987)), or with a Dess-Martin periodinane (1,1,1-triacetoxy-2,1-benzoxiodol-3-(3H)-one) procedure (Edwards et al., U.S. Pat. No. 5,194,588 (1993); Dess & Martin, *J. Org. Chem.*, 48, 4155 (1983)). On-resin trifluoromethyl ketones have been prepared using the modified Pfitzner-Moffat procedure described above.

An alternative strategy is to protect the amino group of the aminotrifluoromethyl alcohol with Boc$_2$O, oxidize the Boc-aminotrifluoromethyl alcohol to the ketone, followed by removal of the Boc group with HBr/HOAc to provide the unprotected trifluoromethyl amino ketone as the HBr salt. In the event an on resin oxidation approach is used, methionine and tryptophane-containing peptides might also be oxidized, but would not be oxidized if the trifluoromethyl amino ketone monomer approach is successful.

There are additional approaches for preparing perfluoroalkyl ketones which involve the addition of metallo perfluoralkyl anions to suitable amino acid derivatives, such as addition of trifluoromethyl zinc to amino acid aldehydes and addition of pentafluoroethyl lithium to protected amino acid esters.

D. Chloromethyl Ketone-based Libraries (—X—Y-Z-CH$_2$—Cl)

Peptide chloromethylketones are traditionally synthesized by coupling a free carboxylic acid to diazomethane using an isobutylchloroformate mixed anhydride procedure, followed by treatment with HCl (FIG. 7) (Schoellmann & Shaw, *Biochem.*, 2, 252 (1963); Green & Shaw, *J. Biol. Chem.*, 256, 1923 (1981)).

Although chloromethyl ketones are unlikely to have clinical application, given their alkylating capability, they form covalent adducts with their targets and have a number of biochemical applications in the study of structure/function relationships in proteins. Chloromethyl ketones are also excellent synthetic intermediates elaborated into a number of interesting protease inhibitor classes, such as hydroxyethylene inhibitors which are effective inhibitors of HIV protease (cf. Dreyer et al., *Biochem.*, 31, 6646 (1992); Konvalinka et al., *Eur. J. Biochem.*, 250, 559 (1997)), and the Alzheimer's disease-related β-secretase enzyme (Shearman et al., *Biochem.*, 39, 8698 (2000), among others.

The proposed method for inverse peptide synthesis has been further refined and can now be used to synthesize peptides with acceptably low levels of racemization. A method for generating inverse peptide trifluoromethyl ketones has been demonstrated and this method is appropriate for library synthesis. One possible route to inverse peptide aldehydes has been tested and found to provide on-resin aldehydes. Resin aldehydes can be protected and eluted from the resin. The method of inverse peptide synthesis is capable of providing a wide variety of C-terminally modified peptide mimetics.

All cited publications, patent applications, and patents are incorporated by reference herein as though fully set forth.

What is claimed is:

1. A method for preparing an immobilized peptide derivative of formula (I):

Sub-[L]-[NH-A-C(O)]$_{n+m}$—OH  (I)

comprising:
(a) reacting an immobilized compound of formula (II):

Sub-(L)-[NH-A-C(O)]$_n$—OH  (II)

with an amino acid ester or peptide derivative of formula (III):

H—[NH-A-C(O)]$_m$—O(tBu)  (III)

in the presence of a coupling agent to yield an immobilized peptide derivative of general formula (IV):

Sub-[L]-[NH-A-C(O)]$_{n+m}$—O(tBu)  (IV);

(b) removing the t-Bu (t-butyl) group to produce an immobilized peptide derivative of general formula (I);
wherein n is a positive integer, m is 1, Sub is a solid support, L is a linker to the amino acid ester or peptide derivative, each NH-A-C(O) independently is the residue of an optionally sidechain-protected amino acid; or the structure —NH-A represents a heterocyclic group.

2. The method of claim 1 which further comprises, prior to step (a): forming an immobilized peptide derivative of general formula (VI):

Sub-[L]-[NH-A-C(O)]$_n$—O(tBu)  (VI);

by reacting a functionalized solid support of general formula Sub[L]X with a compound of formula: H—[NH-A-C(O)]$_n$—O(tBu), wherein X is a group that links L to NH$_2$-A by elimination of XH; and
removing the t-Bu group to yield the immobilized peptide derivative of formula (II).

3. The method of claim 1 or 2 further comprising cleaving the immobilized peptide derivative of formula (IV) at the L-NH bond and removing the t-Bu group to yield a compound of formula (IX);

H- [HN-A-C(O)]$_{n+m}$—OH  (IX).

4. The method of claim 1 further comprising, following step (b); carrying out, x times, the steps of reacting an immobilized peptide derivative of formula (I) with an amino acid ester derivative of formula (III) and removing the t-Bu group to yield an immobilized peptide derivative of formula (VIII):

Sub-(L)-[NH-A-C(O)]$_{n+m(x+1)}$—OH  (VIII)

wherein x is an integer.

5. The method of claim 2 wherein [L]X is —OC(O)(CH$_2$)$_2$CH(NHZ)CO$_2$H, wherein Z is a protecting group.

6. The method of claim 2 wherein [L]X is HNC(O)(CH$_2$)$_2$CH(NHZ)CO$_2$H, wherein Z is a protecting group.

7. The method of claim 5 or 6 wherein Z is benzyloxycarbonyl (Cbz).

8. The method of claim 1 wherein each NH-A-C(O) is individually the optionally sidechain-protected residue of an α-amino acid.

9. The method of claim 1 wherein each NH-A-C(O) is individually the optionally sidechain-protected residue of a naturally occurring L-amino acid.

10. The method of claim 1 wherein the coupling agent is HATU.

11. The method of claim 1 or 2 wherein the t-Bu group is removed with TFA.

12. The method of claim 3 wherein the cleavage is carried out using TFMSA/TFA.

13. The method of claim 3 wherein Sub is a polymer comprising free NH$_2$ or OH groups.

14. The method of claim 13 wherein the polymer comprises polystyrene.

15. The method of claim 1 further comprising reacting an immobilized peptide derivative of formula (I) with H$_2$N(alkyl)CH(OH)CF$_3$ (XV) to yield the corresponding amide of the immobilized peptide derivative of formula (I) and oxidizing the CH(OH) moiety to yield an immobilized peptide derivative of general formula (XII):

Sub-(L)-[NH-A-C(O)]$_{n+m}$—NH(alkyl)C(O)CF$_3$  (XII).

16. The method of claim 15 further comprising cleaving the immobilized peptide derivative of formula (XII) to yield a compound of formula:

H-L-[NH-A-C(O)]$_{n+m}$—NH(alkyl)C(O)CF$_3$.

17. The method of claim 4 further comprising reacting the immobilized peptide derivative of formula (VIII) with compound (XV) to yield the corresponding amide of the immobilized peptide derivative of formula (VIII) and oxidizing the CH(OH) moiety to yield an immobilized peptide derivative of general formula (XVI):

Sub-(L)-[NH-A-C(O)]$_{n+m(x+1)}$—NH(alkyl)C(O)CF$_3$  (XVI).

18. The method of claim 17 further comprising cleaving compound (XVI) from Sub to yield a compound of formula:

H-L-[NH-A-C(O)]$_{n+m(x-1)}$—NH(alkyl)C(O)CF$_3$.

19. The method of claim 1 further comprising reacting the immobilized peptide derivative of formula (I) with H$_2$N (alkyl)OH (XVII) to yield the hydroxyalkylamide of (I) and oxidizing the terminal hydroxy group to yield an immobilized peptide derivative of formula (XIII):

Sub-(L)-[NH-A-C(O)]$_{n+m}$—NH(alkyl)CHO     (XIII).

20. The method of claim 4 further comprising reacting the immobilized peptide derivative of formula (VIII) with H$_2$N(alkyl)OH (XVII) to yield the hydroxyalkylamide of (VIII) and oxidizing the terminal hydroxyl group to yield the immobilized peptide derivative of formula (XVIII):

Sub-(L)-[NH-A-C(O)]n+m(x+1)—NH(alkyl)CHO     (XVIII).

21. The method of claim 19 further comprising protecting the terminal CHO group of the immobilized peptide derivative of formula (XIII).

22. The method of claim 20 further comprising protecting the terminal CHO group of the immobilized peptide derivative of formula (XVIII).

23. The method of claim 21 or 22 wherein the CHO group of the immobilized peptide compound of formula XIII or of formula XVIII is converted into an ethylene glycol acetal, a propylene glycol acetal, an ethylene dithiol acetal or a 1,3-dithiane.

24. The method of claim 23 further comprising cleaving the immobilized peptide derivative wherein the CHO group is converted into an ethylene glycol acetal, a propylene glycol acetal, an ethylene dithiol acetal or a 1,3-dithiane to yield a compound of formula:

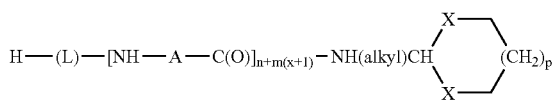

wherein each X is O or each X is S, and p is 0 or 1.

25. The method of claim 4 further comprising reacting an immobilized peptide derivative of formula (VIII) with a boroamine to yield an immobilized peptide derivative of formula (XIV):

Sub-[L]-[NH-A-C(O)]$_{n+m(x+1)}$—NH(A)B(OR)$_2$     (XIV), wherein R is (C$_1$–C$_6$)alkyl, phenyl, or the residue of a diol and wherein NH(A)B(OR)$_2$ is the residue of an O-protected aminoboronic acid.

26. The method of claim 1 further comprising reacting an immobilized peptide derivative of formula (I) with a boroamine to yield a compound of fonnula (XIX):

Sub-[L]-[NH-A-C(O)]$_{n+m}$—NH(A)B(OR)$_2$     (XIX), wherein R is (C$_1$–C$_6$)alkyl, phenyl, or the residue of a diol and wherein NH(A)B(OR)$_2$ is the residue of an O-protected aminoboronic acid.

27. The method of claim 25 further comprising cleaving compound (XIV) to yield a compound of formula:

H-[L]-[NH-A-C(O)]$_{n+m(x+1)}$—NH(A)B(OH)$_2$.

28. The method of claim 26 further comprising cleaving compound (XIX) to yield a compound of formula:

H-[L]-[NH-A-C(O)]$_{n+m}$—NH(A)B(OH)$_2$.

29. The method of claim 1 or 2 wherein n is 1.
30. The method of claim 4 wherein x is 1–10.
31. The method of claim 30 wherein x is 1–5.
32. The method of claim 2 wherein [L]X is —OC(O)(CH$_2$)$_2$CO$_2$H.
33. The method of claim 1 wherein at least one NH-A-C(O) comprises a residue of proline or hydroxyproline.

* * * * *